United States Patent
Li

(10) Patent No.: US 10,353,104 B2
(45) Date of Patent: Jul. 16, 2019

(54) CARBONATE PERMEABILITY BY PORE TYPING

(75) Inventor: Lilong Li, Humble, TX (US)

(73) Assignee: BAKER HUGHES, A GE COMPANY, LLC, Houston, TX (US)

(*) Notice: Subject to any disclaimer, the term of this patent is extended or adjusted under 35 U.S.C. 154(b) by 713 days.

(21) Appl. No.: 13/433,570

(22) Filed: Mar. 29, 2012

(65) Prior Publication Data

US 2013/0261973 A1 Oct. 3, 2013

(51) Int. Cl.
| | | |
|---|---|---|
| G01V 5/04 | (2006.01) |
| G01V 3/14 | (2006.01) |
| G06F 19/00 | (2018.01) |
| G01V 3/32 | (2006.01) |
| G01N 24/08 | (2006.01) |

(52) U.S. Cl.
CPC .......... G01V 3/14 (2013.01); G01N 24/081 (2013.01); G01V 3/32 (2013.01); G06F 19/00 (2013.01)

(58) Field of Classification Search
CPC ...................................................... G01V 3/14
See application file for complete search history.

(56) References Cited

U.S. PATENT DOCUMENTS

| | | | | |
|---|---|---|---|---|
| 4,344,142 A | * | 8/1982 | Diehr et al. ................. 700/198 |
| 5,289,124 A | * | 2/1994 | Jerosch-Herold et al. ... 324/303 |
| 5,387,865 A | * | 2/1995 | Jerosch-Herold et al. ... 324/303 |
| 5,497,087 A | * | 3/1996 | Vinegar et al. ............... 324/303 |
| 6,005,389 A | * | 12/1999 | Prammer ...................... 324/303 |
| 6,088,656 A | | 7/2000 | Ramakrishnan et al. |
| 6,344,744 B2 | * | 2/2002 | Taicher et al. ................ 324/303 |
| 6,366,087 B1 | * | 4/2002 | Coates et al. ................. 324/303 |
| 6,573,715 B2 | * | 6/2003 | King et al. .................... 324/303 |
| 6,686,736 B2 | * | 2/2004 | Schoen et al. ................ 324/303 |
| 6,714,841 B1 | | 3/2004 | Wright et al. |
| 6,959,246 B2 | * | 10/2005 | Herron ............................ 702/12 |
| 6,977,499 B2 | | 12/2005 | Kiesl et al. |
| 6,987,385 B2 | | 1/2006 | Akkurt et al. |
| 2003/0120151 A1 | * | 6/2003 | Constantinides ............. 600/431 |
| 2005/0168220 A1 | * | 8/2005 | Lenormand et al. ......... 324/303 |
| 2007/0047117 A1 | * | 3/2007 | Wang .................. G01N 24/081 |
| | | | 359/879 |
| 2007/0052551 A1 | * | 3/2007 | Lovell ................. G01V 11/002 |
| | | | 340/854.6 |
| 2010/0277167 A1 | * | 11/2010 | Romero ....................... 324/303 |

OTHER PUBLICATIONS

US Supreme Court Decision (*Alice* vs *CLS Bank*) (2013).*
Magritek, "Routine Core Analysis, Pore size distributions".*

(Continued)

*Primary Examiner* — Hyun D Park
(74) *Attorney, Agent, or Firm* — Cantor Colburn LLP

(57) ABSTRACT

A method for estimating a property of an earth formation includes: conveying a carrier through a borehole penetrating the earth formation; performing nuclear magnetic resonance (NMR) measurements on a sensitive volume in the formation using an NMR tool disposed at the carrier to provide a distribution of relaxation times; identifying peaks in the distribution of relaxation times; selecting at least one peak based on a characteristic of the at least one peak; and estimating the property using a relaxation time associated with the at least one peak.

14 Claims, 4 Drawing Sheets

(56) References Cited

OTHER PUBLICATIONS

N. Gomma, et al. Case Study of Permeability, Vug Quantification, and Rock Typing in a Complex Carbonate, Society of Petroleum Engineers, SPE 102888, Sep. 24-27, 2006, pp. 1-10, San Antonio, Texas.
S. Frank, Carbonate Rock Typing Using NMR Data: A Case Study From Al Shaheen Field, Offshore Qatar, International Petroleum Technology Conference (IPTC 10889), Nov. 21-23, 2005, pp. 1-14, Doha, Qatar.
T.S. Ramakrishnan, A Model-Based Interpretation Methodology for Evaluating Carbonate Reservoirs, Society of Petroleum Engineers, SPE 71704, Oct. 3, 2001, pp. 1-15, New Orleans, Louisiana.

* cited by examiner

CARBONATE PERMEABILITY BY PORE TYPING

BACKGROUND

Boreholes are drilled deep into the earth for many applications such as hydrocarbon exploration, geothermal production, and carbon dioxide sequestration. Different types of measurements are usually performed on a geologic formation in order to efficiently use production resources. One type of important measurement is permeability. Permeability relates to a measurement of the ability of a rock to transmit fluids generally through connected pores. Permeability is determined from the pore sizes that can transmit fluid and is usually measured using a nuclear magnetic resonance (NMR) tool disposed in a borehole penetrating the geologic formation Carbonate is one type of geologic formation of interest. The pore system in carbonate formations is usually heterogeneous, yet such heterogeneity does not mean that different types of pores all contribute to fluid flow significantly. For example, in a micro-interparticle dual porosity formation, the fluid flows mainly through interparticle pores and the microporosity can be ignored in a permeability calculation. In an interparticle-vugg dual porosity formation, if the amount of vuggy porosity is not high, simulation can show that the permeability is not altered that much because of the presence of vuggy porosity.

In order to treat different types of pores differently, it is necessary to do pore typing. Typically, in prior art NMR logging interpretation, pore typing is done with NMR relaxation time cut-off values applied universally. The universally applied cut-off values divided the pores into macro-, meso-, and micro-sized pores. Coates and SDR equations are adapted to a hybrid set of equations such that one equation covers the high permeability part of the formation and the other equation covers the low permeability part of the formation. Unfortunately, pore typing based on universally applied sizes has limitations in resolving the true carbonate characteristics in complex carbonate formations, each with a distinct set of pores present. By relying on universally applied pore sizes, the prior art NMR logging interpretation may fail to predict permeability accurately. Hence, it would be appreciated in the drilling industry if techniques to determine formation permeability could be improved.

BRIEF SUMMARY

Disclosed is a method for estimating a property of an earth formation. The method includes conveying a carrier through a borehole penetrating the earth formation and performing nuclear magnetic resonance (NMR) measurements on a sensitive volume in the formation using an NMR tool disposed at the carrier to provide a distribution of relaxation times. The method further includes identifying peaks in the distribution of relaxation times, selecting at least one peak from the identified peaks using a characteristic of the at least one peak, and estimating the property using a relaxation time associated with the at least one peak.

Also disclosed is an apparatus for estimating a property of an earth formation. The apparatus includes a carrier configured to be conveyed through a borehole penetrating the earth formation, a nuclear magnetic resonance (NMR) tool disposed at the carrier and configured to perform NMR measurements on a sensitive volume in the formation to provide a distribution of relaxation times, and a processor coupled to the NMR tool. The processor is configured to identify peaks in the distribution of relaxation times, determine an area under each identified peak, select at least one peak based on the determined area of the at least one peak using the determined peak areas; and estimate the property using a relaxation time associated with the at least one peak.

Further disclosed is a non-transitory computer-readable medium having computer executable instructions for estimating a property of an earth formation by implementing a method that includes: receiving a distribution of relaxation times from a nuclear magnetic resonance (NMR) tool that performed NMR measurements on a sensitive volume in the formation; identifying peaks in the distribution of relaxation times; selecting at least one peak based on a characteristic of the at least one peak; and estimating the property using a relaxation time associated with the at least one peak.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures.

Disclosed are apparatus and method for estimating permeability of an earth formation with improved accuracy using nuclear magnetic resonance (NMR) data obtained from an NMR tool. Improved accuracy derives from using a pore model customized for each formation logged by the NMR tool. Statistically distinguishable peaks in size distribution of pores are considered as separate types of pores in the rock formation. Depending on the shape and relative weight of the peaks, the pore types that contribute to the majority of the fluid flow are selected and the average size of these pore types are computed. The permeability is then calculated using the average size of these selected pore types.

Figure 1:
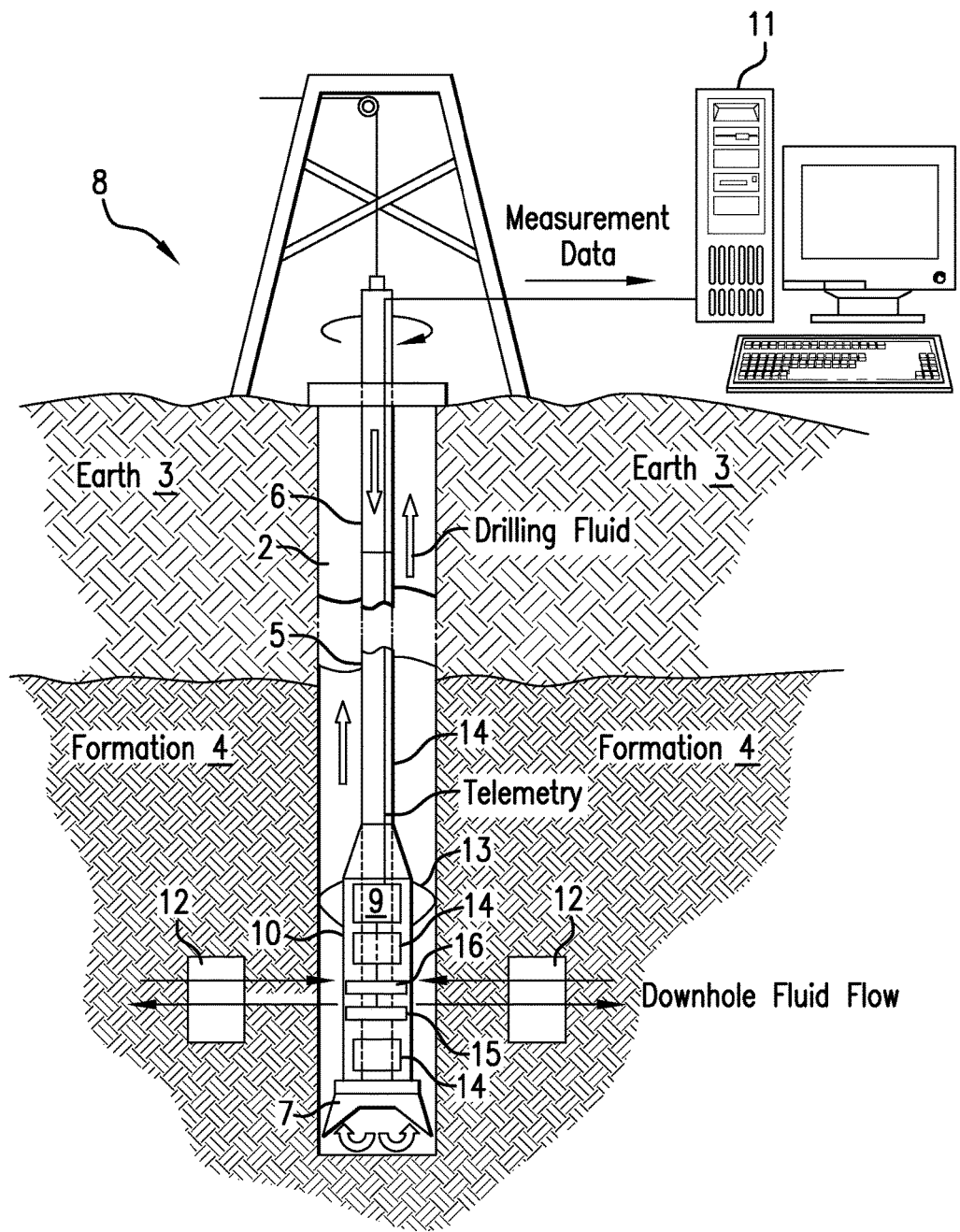
FIG. 1 illustrates an exemplary embodiment of a downhole tool disposed in a borehole penetrating the earth.

FIG. 1 illustrates a cross-sectional view of an exemplary embodiment of a nuclear magnetic resonance (NMR) tool 10 disposed in a borehole 2 penetrating the earth 3, which includes an earth formation 4. The formation 4 represents any subsurface material of interest. The NMR tool 10 is coupled to a carrier 5 and is conveyed through the borehole 2 by the carrier 5. In the embodiment of FIG. 1, the carrier 5 is a drill string 6 in an embodiment known as logging-while-drilling (LWD). Disposed at a distal end of the drill string 6 is a drill bit 7. A drilling rig 8 is configured to conduct drilling operations such as rotating the drill string 6 and thus the drill bit 7 in order to drill the borehole 2. In addition, the drilling rig 8 is configured to pump drilling fluid through the drill string 6 in order to lubricate the drill bit 7 and flush cuttings from the borehole 2. In one or more embodiments, a stabilizer 13 may be used to limit lateral movement of the NMR tool 10 in the borehole 2. Downhole electronics 9 are configured to operate the NMR tool 10 and/or process measurements or data received from the tool 10. Telemetry is used to provide communications between the NMR tool 10 and a computer processing system 11 disposed at the surface of the earth 3. NMR data processing or operations can also be performed by the computer processing system 11 in addition to or in lieu of the downhole electronics 9. The NMR tool 10 may operate intermittently, at particular intervals, or continuously during the drilling process to provide NMR data for various depths in the borehole 2 and, thus, in the formation 4. In an alternative embodiment, the carrier 5 can be an armored wireline in an embodiment known as wireline logging.

The NMR tool 10 includes NMR components configured to perform NMR measurements on a sensitive volume 12 in the formation 4. The sensitive volume 12 has a generally toroidal shape surrounding the borehole 2. The NMR components include an arrangement of magnets 14 that is configured to generate a static magnetic field having a decreasing field strength or magnitude with increasing radial distance from the NMR tool in the sensitive volume 12. A radio frequency (RF) coil 15 or antenna is used to produce pulsed RF fields substantially orthogonal to the static field in the sensitive volume 12. The nuclear spins in the sensitive volume 12 align themselves partly along the static magnetic field, applied by the magnets 14, forming a macroscopic nuclear magnetization. A pulsed RF field is applied to tip the nuclear magnetization into the transverse plane, resulting in a precession of the magnetization. Such a tipping pulse is followed by a series of refocusing pulses and the resulting series of pulse echoes (also referred to as spin echoes or NMR signals) is detected by a receiver coil 16 or antenna.

The pulse sequences may be in the form of a Carr-Purcell-Meiboom-Gill (CPMG) sequence or, alternatively, an optimized rephasing pulse sequence (ORPS). ORPS is similar to CPMG but the pulse widths are optimized for the actual field distributions of the static and alternating fields. The alternative sequence may be used to maximize signal and minimize RF power consumption. The NMR signals include a longitudinal relaxation time constant (referred to as $T_1$) and a transverse relaxation time constant (referred to as $T_2$). The term "relaxation" relates to the nuclear magnetization precessing towards equilibrium. From the NMR signals, a distribution of transverse relaxation time constants (referred to as a $T_2$ distribution) is obtained. The $T_2$ distribution relates amplitude to $T_2$ or a function of $T_2$ such as a logarithmic function.

Figure 2:
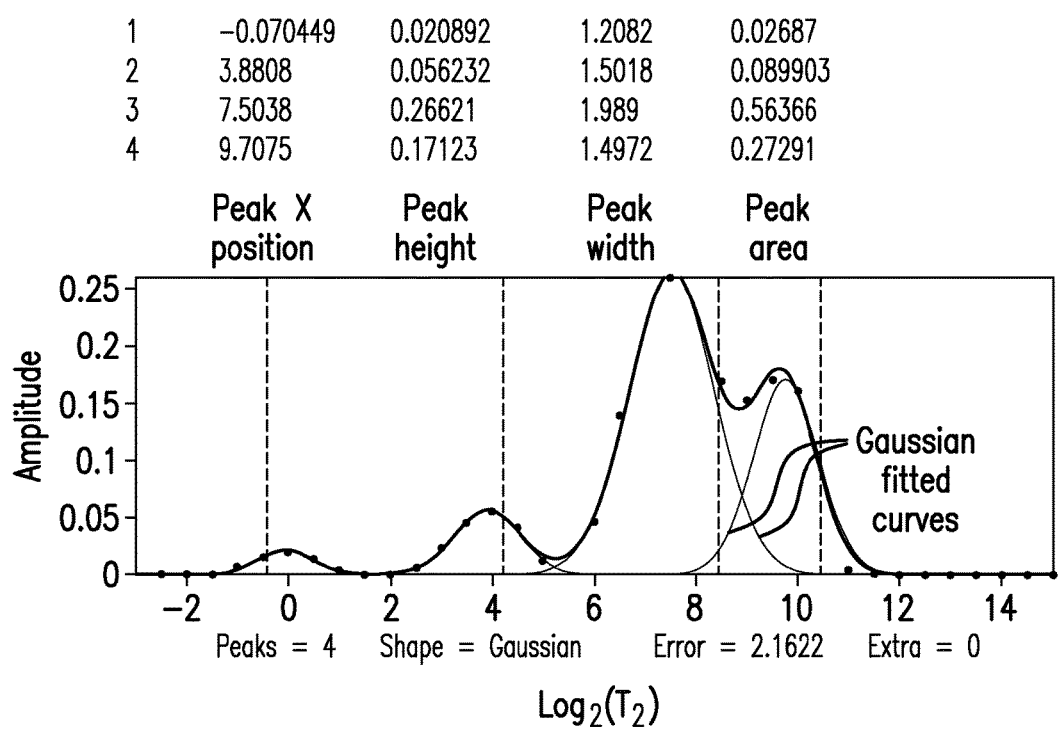
FIG. 2 illustrates a distribution of NMR transverse relaxation decay time constants.

One way of obtaining pore size distribution is to look at the NMR $T_2$ distribution. FIG. 2 illustrates a NMR $T_2$ spectrum having four distinct peaks where amplitude is plotted on the vertical axis and $Log_2(T_2)$ is plotted on the horizontal axis. Each of the peaks is fit with a Gaussian curve. The peak with the maximum underlying area is then easily found. Depending on the shape and relative position of the peaks, one or more peaks are selected to compute the average position of the peaks (and, hence, average pore size) and the overall underlying area of these peaks. As one processing example, if the neighboring or adjacent peaks have more than 60% of the area of the maximum peak, those peaks are included in the calculation of average pore size and the overall area under the associated Gaussian curves.

From the overall area under the selected peaks, one can compute the corresponding porosity using Equation (1).

$$\phi_{ave} = \phi_T \frac{S_{ave}}{S_T} \quad (1)$$

In Equation (1), $\phi_{ave}$ is the porosity corresponding to those peaks selected for inclusion, $S_{ave}$ is the total area corresponding to the peaks selected for inclusion, $\phi_T$ is the total porosity, and $S_T$ is the total area of all the peaks.

The log-mean of the $T_2$ for the included peaks is computed according to Equation (2).

$$T2_{ave} = 2^{\Sigma_i(\log_2 T2_i)*\phi_i/\Sigma_i\phi_i} \quad (2)$$

In Equation (2), $T2_{ave}$ is the average $T_2$ value corresponding to those peaks selected for inclusion. The summations are done over those peaks. The porosity for peak i, $\phi_i$, is calculated the same way as $\phi_{ave}$ $$\left(\text{i.e., } \phi_i = \phi_T \frac{S_i}{S_T}\right),$$

and $T2_i$ is the $T_2$ reading at the middle of the corresponding Gaussian peak.

Using the $T2_{ave}$ calculated in Equation (2), the permeability is then calculated using Equation (3).

$$k = a\phi_{ave}^2(\rho T2_{ave})^2 \quad (3)$$

In Equation (3), k is the permeability, $\rho$ is the surface relaxivity, and a is a constant.

Figure 3:
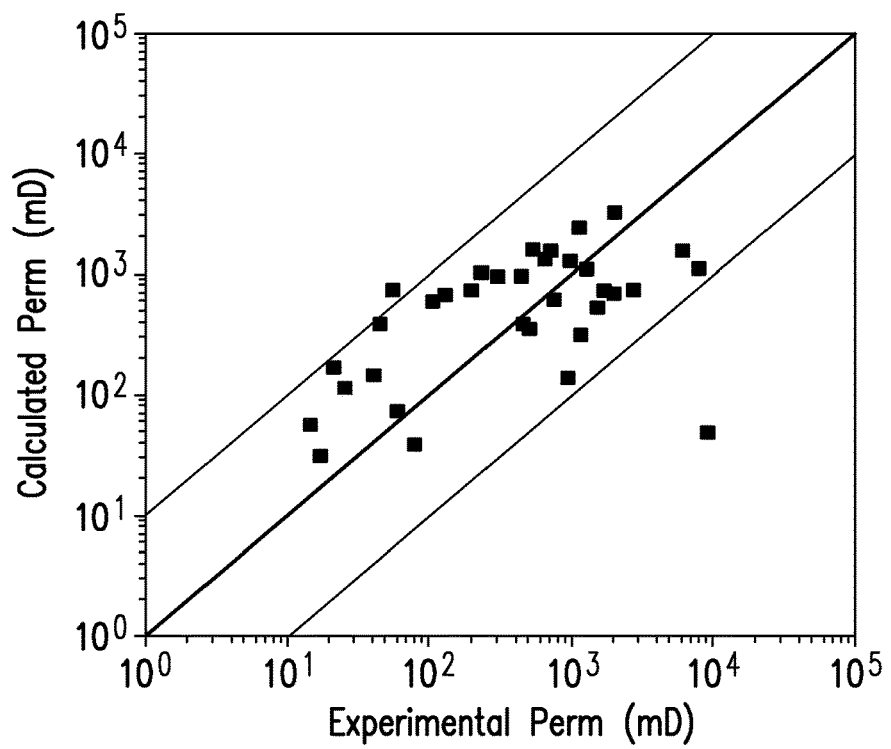
FIG. 3 illustrates a comparison of calculated permeability using the techniques disclosed herein to experimentally determine permeability for 35 carbonate samples.
Figure 4:
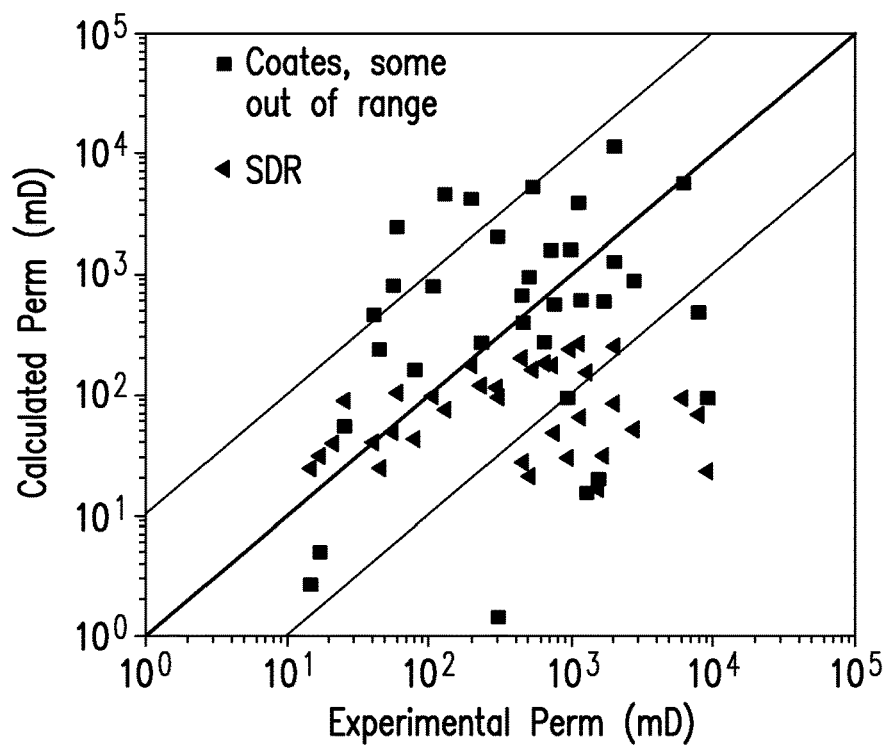
FIG. 4 illustrates a comparison of calculated permeability using prior art techniques to experimentally determine permeability for 35 carbonate samples.

FIG. 3 illustrates the results of calculations using the above equations for 35 carbonate samples varying from floatstones to dolostones, grainstones and wachestones. The center diagonal line represents an exact match, while the two other diagonal lines represent a one order of magnitude error. FIG. 4 illustrates the results of calculations using the prior art technique of universal pore typing (i.e., applying a set of universal cut-off values to estimate pore types). As with FIG. 3, the center diagonal line in FIG. 4 represents an exact match, while the two other diagonal lines represent a one order of magnitude error. As can be seen by comparing FIG. 3 to FIG. 4, there are genuine improvements to permeability calculations using the equations and calculation techniques disclosed herein.

Figure 5:
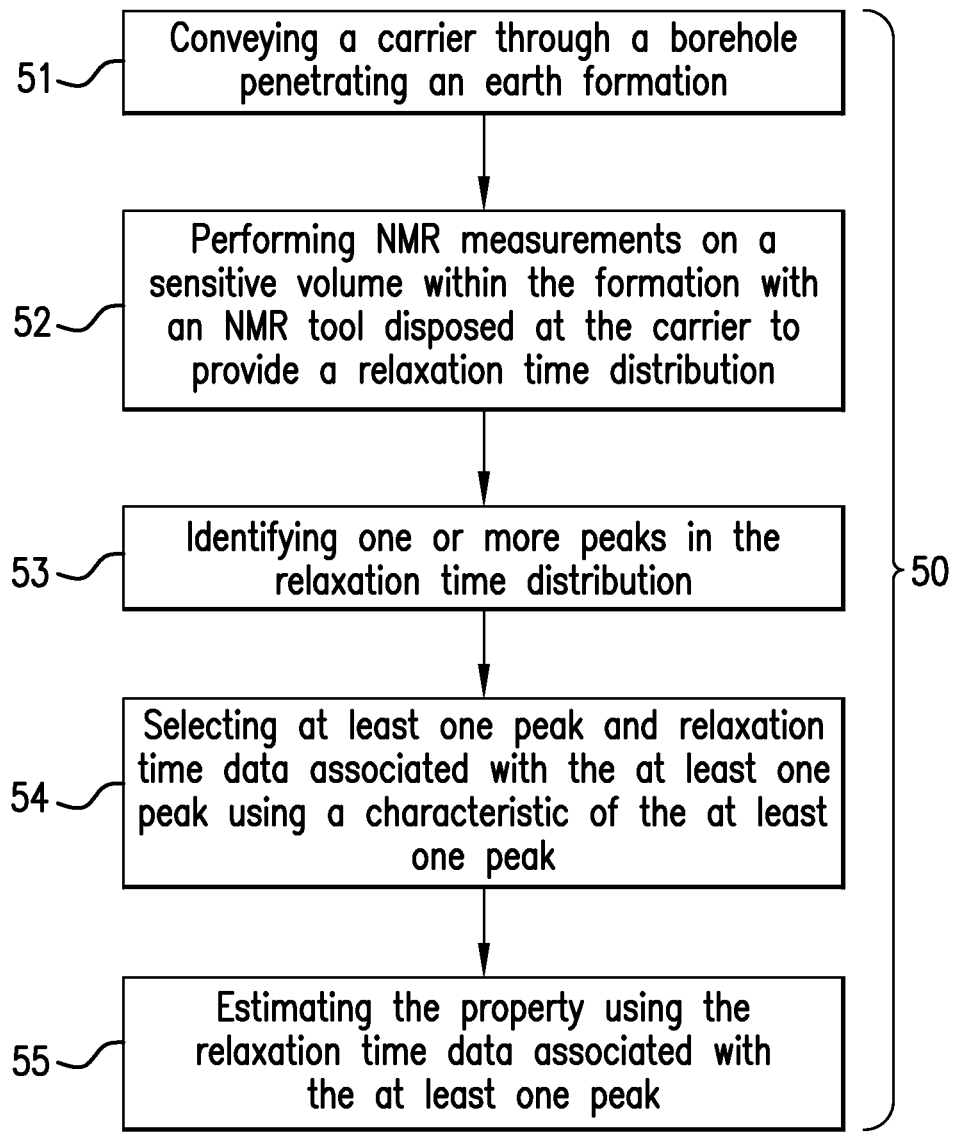
FIG. 5 illustrates a flow chart for a method for calculating permeability of an earth formation.

FIG. 5 is a flow chart for a method 50 for estimating a property of an earth formation. Block 51 calls for conveying a carrier through a borehole penetrating the formation. Block 52 calls for performing NMR measurements on a sensitive volume within the formation with an NMR tool disposed at the carrier to provide a relaxation time distribution. The NMR measurements are generally performed at a plurality of depths in the borehole such that the estimated property corresponds to the plurality of depths in the formation. Block 53 calls for identifying one or more peaks in the relaxation time distribution. Block 54 calls for selecting at least one peak from the identified peaks using a characteristic of the at least one peak. This block can include determining an area under each of the identified peaks where the peak area is a characteristic used for the selecting. This block can also include fitting a Gaussian curve to each of the identified peaks and determining the area under each Gaussian curve as the peak area. Further, this block can include selecting the peak having the largest area and one or more other peaks meeting one or more selection criteria. One selection criterion may be that the one or more other peaks are adjacent to the peak having the largest area. Another selection criterion may be selecting those peaks having an area that meets or exceeds a percentage of the area of the peak having the largest area. Block 55 calls for estimating the property using the relaxation time data associated with the at least one peak. In one or more non-limiting embodiments, the relaxation time associated with each peak is the relaxation time at the middle of the Gaussian curve or at a center of gravity of the area of the selected peak. The property in one or more embodiments is permeability.

In support of the teachings herein, various analysis components may be used, including a digital and/or an analog system. For example, the downhole electronics 9 or the surface computer processing 11. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order. The term "couple" relates to coupling a first component to a second component either directly or indirectly through an intermediate component.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a permeability of an earth formation, the method comprising:
   conveying a carrier through a borehole penetrating the earth formation;
   performing nuclear magnetic resonance (NMR) measurements on a sensitive volume in the formation using an NMR tool disposed at the carrier to provide a distribution of relaxation times;
   identifying peaks in the distribution of relaxation times;
   determining an area under each identified peak;
   selecting a peak having a maximum underlying area from the identified peaks;
   selecting a plurality of other peaks from the identified peaks using a selection criterion, wherein the selection criterion comprises selecting a peak that is adjacent to the peak having the maximum underlying area and the adjacent peak has an area that meets or exceeds a threshold;
   averaging the relaxation times for the peak having a maximum underlying area and the plurality of other peaks to provide an average relaxation time;
   estimating the permeability using the average relaxation time; and
   transmitting a signal comprising the estimated permeability to a signal receiving device comprising a user interface or a storage medium, wherein the identifying, selecting a peak, selecting a plurality of other peaks, averaging, estimating and transmitting are performed using a processor coupled to the NMR tool.

2. The method according to claim 1, wherein the NMR measurements are performed at a plurality of depths in the borehole.

3. The method according to claim 1, wherein the selection criterion relates to the area under each of the peaks in the plurality.

4. The method according to claim 3, wherein identifying comprises fitting a curve to each of the identified peaks.

5. The method according to claim 4, wherein the curve is a Gaussian curve.

6. The method according to claim 4, wherein determining comprises determining an area under the fitted curve for each identified peak.

7. The method according to claim 1, wherein estimating the property using the average relaxation time comprises using $T_{2ave}$ calculated as $$\Sigma_i (\log_2 T2_i) * Q_i / \Sigma_i Q_i$$

$T2_{ave}=2$ where $\Sigma_i$ is a summation over i peaks, $T_{2i}$ is a $T_2$ reading within the i-th peak, and $$\phi_i = \phi_T \frac{S_i}{S_T}$$

where $\phi_t$ is total porosity for the i peaks, $S_i$ is the area under the i-th peak, and $S_T$ is a total area under all of the selected peaks.

8. The method according to claim 7, wherein the $T_2$ reading is at a center of gravity of the i-th peak.

9. The method according to claim 7, wherein the $T_2$ reading is at a middle of a Gaussian curve fitted to the i-th peak.

10. An apparatus for estimating a permeability of an earth formation, the apparatus comprising:
 a carrier configured to be conveyed through a borehole penetrating the earth formation;
 a nuclear magnetic resonance (NMR) tool disposed at the carrier and configured to perform NMR measurements on a sensitive volume in the formation to provide a distribution of relaxation times;
 a processor coupled to the NMR tool and configured to:
  identify peaks in the distribution of relaxation times;
  determine an area under each identified peak;
  select a peak having a maximum underlying area from the identified peaks;
  select a plurality of other peaks from the identified peaks using a selection criterion, wherein the selection criterion comprises selecting a peak that is adjacent to the peak having the maximum underlying area and the adjacent peak has an area that meets or exceeds a threshold; and
  average the relaxation times for the peak having a maximum underlying area and the plurality of other peaks to provide an average relaxation time;
  estimate the permeability using the average relaxation time.

11. The apparatus according to claim 10, wherein the property is permeability.

12. The apparatus according to claim 10, wherein the NMR measurements are performed at a plurality of depths in the borehole.

13. The apparatus according to claim 10, wherein the carrier comprises a wireline, a slickline, a drill string, or coiled tubing.

14. A method for efficiently using a production resource to produce hydrocarbons based on estimating a permeability of an earth formation that includes a carbonate, the method comprising:
 conveying a carrier through a borehole penetrating the earth formation comprising a carbonate;
 performing nuclear magnetic resonance (NMR) measurements on a sensitive volume in the formation comprising a carbonate using an NMR tool disposed at the carrier to provide a distribution of relaxation times;
 identifying peaks in the distribution of relaxation times;
 determining an area under each identified peak;
 selecting a peak having a maximum underlying area from the identified peaks;
 selecting a plurality of other peaks from the identified peaks using a selection criterion, wherein the selection criterion comprises selecting a peak that is adjacent to the peak having the maximum underlying area and the adjacent peak has an area that meets or exceeds a threshold; and
 averaging the relaxation times for the peak having a maximum underlying area and the plurality of other peaks to provide an average relaxation time;
 estimating the permeability using the average relaxation time, wherein the identifying, selecting a peak, selecting a plurality of other peaks, averaging, and estimating are performed using a processor coupled to the NMR tool; and
 using the production resource to produce hydrocarbons based on the estimated permeability.

* * * * *